United States Patent
Okonski-Fernandez et al.

(10) Patent No.: US 10,675,220 B2
(45) Date of Patent: Jun. 9, 2020

(54) CLEAN ENVIRONMENT FOR MIXING INJECTABLE DRUGS

(71) Applicants: Irene Gabriela Okonski-Fernandez, Richmond, CA (US); Deborah Zerda-Andrews, San Rafael, CA (US)

(72) Inventors: Irene Gabriela Okonski-Fernandez, Richmond, CA (US); Deborah Zerda-Andrews, San Rafael, CA (US)

( * ) Notice: Subject to any disclaimer, the term of this patent is extended or adjusted under 35 U.S.C. 154(b) by 161 days.

(21) Appl. No.: 15/932,088

(22) Filed: Feb. 2, 2018

(65) Prior Publication Data

US 2019/0240112 A1    Aug. 8, 2019

(51) Int. Cl.
| | | |
|---|---|---|
| *A61J 1/10* | (2006.01) | |
| *A61J 1/16* | (2006.01) | |
| *A61B 50/36* | (2016.01) | |
| *A61B 50/37* | (2016.01) | |
| *A61J 1/20* | (2006.01) | |
| *A61B 50/10* | (2016.01) | |

(52) U.S. Cl.
CPC .............. *A61J 1/16* (2013.01); *A61B 50/362* (2016.02); *A61B 50/37* (2016.02); *A61J 1/2003* (2015.05); *A61B 2050/105* (2016.02); *A61J 1/10* (2013.01); *A61J 2205/30* (2013.01)

(58) Field of Classification Search
CPC ......... A61B 50/30; A61B 50/33; A61B 50/34; A61B 50/37; A61B 50/362; A61J 1/10; A61J 1/16; A61J 1/20; A61J 1/2003; A61J 1/2093; A61J 2205/30
USPC ........................... 604/82, 403, 408, 414, 416
See application file for complete search history.

(56) References Cited

U.S. PATENT DOCUMENTS

| 3,872,868 | A | * | 3/1975 | Kline | A61J 1/05 604/403 |
|---|---|---|---|---|---|
| 4,463,876 | A | * | 8/1984 | Swallert | A47K 5/1215 222/105 |
| 4,976,851 | A | * | 12/1990 | Tanokura | A61M 1/029 210/109 |
| 5,262,070 | A | * | 11/1993 | Ishida | A61M 1/029 100/211 |
| 6,663,829 | B1 | * | 12/2003 | Kjellstrand | A61J 1/2093 206/219 |
| 8,678,236 | B2 | * | 3/2014 | Burke | B67D 7/0216 222/101 |
| 2005/0133674 | A1 | * | 6/2005 | Sobue | A61J 1/16 248/95 |
| 2005/0159784 | A1 | * | 7/2005 | Arceta | A61G 12/001 607/20 |

(Continued)

FOREIGN PATENT DOCUMENTS

| EP | 608882 A1 | * | 8/1994 |
|---|---|---|---|
| EP | 611579 A1 | * | 8/1994 |

*Primary Examiner* — Joshua E Rodden

(57) ABSTRACT

A clean environment for mixing injectable drugs having a floor and back member made of stainless steel that is L shaped when seen from the side. The base portion sits on top of a drawer assembly. The back portion has accessory retaining compartments mounted on the left and right side that hold accessories necessary for the process of injecting drugs into IV bags. An IV tip holder is magnetically held to the base portion. Integral posts are located on the top portion of the back member to removably retain the end of a standard IV bag. A circular cutout on the base portion allows for the insertion of a plastic cup.

5 Claims, 4 Drawing Sheets

(56) References Cited

U.S. PATENT DOCUMENTS

| | | | | |
|---|---|---|---|---|
| 2006/0245980 A1* | 11/2006 | Kiselev | .................... | A61J 3/00 |
| | | | | 422/130 |
| 2010/0174415 A1* | 7/2010 | Humayun | ............... | A61B 50/13 |
| | | | | 700/282 |
| 2011/0034899 A1* | 2/2011 | Thome, Jr. | ................ | A61J 1/16 |
| | | | | 604/407 |
| 2014/0014538 A1* | 1/2014 | Dawson | ............. | B65D 83/0409 |
| | | | | 206/216 |
| 2015/0175307 A1* | 6/2015 | Okuma | .................... | A61J 1/16 |
| | | | | 414/416.01 |
| 2016/0338760 A1* | 11/2016 | Houser | ................. | A61B 34/25 |

* cited by examiner

CLEAN ENVIRONMENT FOR MIXING INJECTABLE DRUGS

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of hospital room accessories and more specifically to a clean environment housing for mixing injectable drugs.

In caring for patients with various illnesses, it is sometimes necessary to inject and intravenous drip (IV) into a patient to supply a continuous amount of a particular medication or medications. Traditionally, a flexible bag, known as an IV bag containing the liquid medication is suspended on an IV pole near the patient and a flexible tube extends from the IV bag to an injectable needle that is inserted through the skin of the patient's arm or other body part. For many procedures, the contents of the IV bag are prepared in a pharmacy and then transported to the end use location such as a hospital room. In these cases, the pharmacist injects the contents of the IV bag in a germ free clean environment that is created by the use of a laminar flow hood which directs fan propelled filtered clean air into the area under the hood thereby eliminating the possibility of air borne contaminants to be present during the process of injecting the medication into the IV bag. Horizontal laminar flow hoods such as the BZ series manufactured by Germfree Inc of Ormond Beach Fla. are generally made of stainless steel and cost thousands of dollars to purchase.

Although these types of hoods are well suited to a pharmacy environment where there is sufficient space and purchasing power to allow ownership of such a hood, they are not financially or spatially suited to a hospital emergency room environment where an IV bag must be prepared quickly and within a relatively small space that has not been specifically designed for such activity. Typically, a space on a work surface is marked off by tape and designated as the IV bag injection zone. The zone is supposed to be cleaned regularly and items that are commonly used during the injection procedure should be within easy reach. However, due to the busy and sometimes chaotic nature of emergency room environments, the IV injection zone may not meet the above stated requirements.

Furthermore, the current pharmacy grade laminar flow hood systems to not include a spring clip for holding the injectable portion of the bag in place allowing the user to inject the medication with one hand and without the need to hold onto the flexible injectable portion with the other hand. Additionally, the current laminar hood flow systems to not include a magnetically attachable IV bag holder that can be placed anywhere on the horizontal surface of the IV bag injection zone allowing it to be placed perfectly for either a right handed or left handed person.

BRIEF SUMMARY OF THE INVENTION

The primary object of the invention is to provide portable a clean environment for mixing injectable drugs.

Another object of the invention is to provide clean environment for mixing injectable drugs that includes storage areas for many of the commonly used items associated with the process of injecting IV bags with drugs.

Another object of the invention is to provide a clean environment that includes a magnetically attachable IV bag tip holding assembly that allows the user to easily engage the injectable portion of the bag using only one hand.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed a clean environment assembly for mixing injectable drugs comprising: a main L shaped floor and back wall member, a plurality of holding compartments for removably retaining common items associated with the process of injecting IV pouches, a magnetically attached IV tip support member, a drawer member, a hinge, a gasket, said L shaped floor and back member made from stainless steel, said holding compartments attached to either side of said L shaped floor and back member, said floor and back member including a means to removably retain the rear end of said IV bag, said floor and back member also including a circular cutout for removably retaining a standard one ounce plastic cup.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
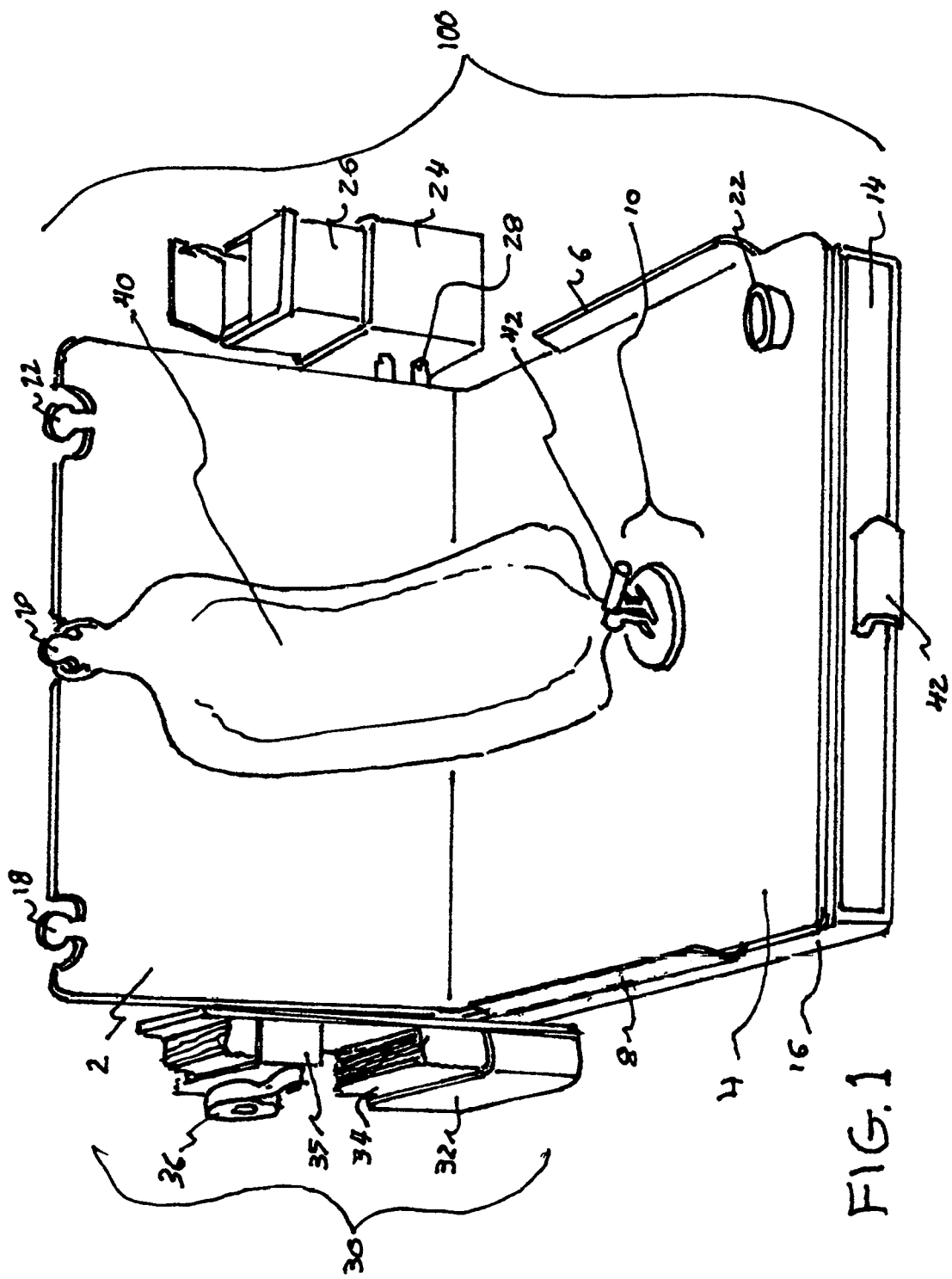
FIG. 1 is a perspective view of the invention.
Figure 3:
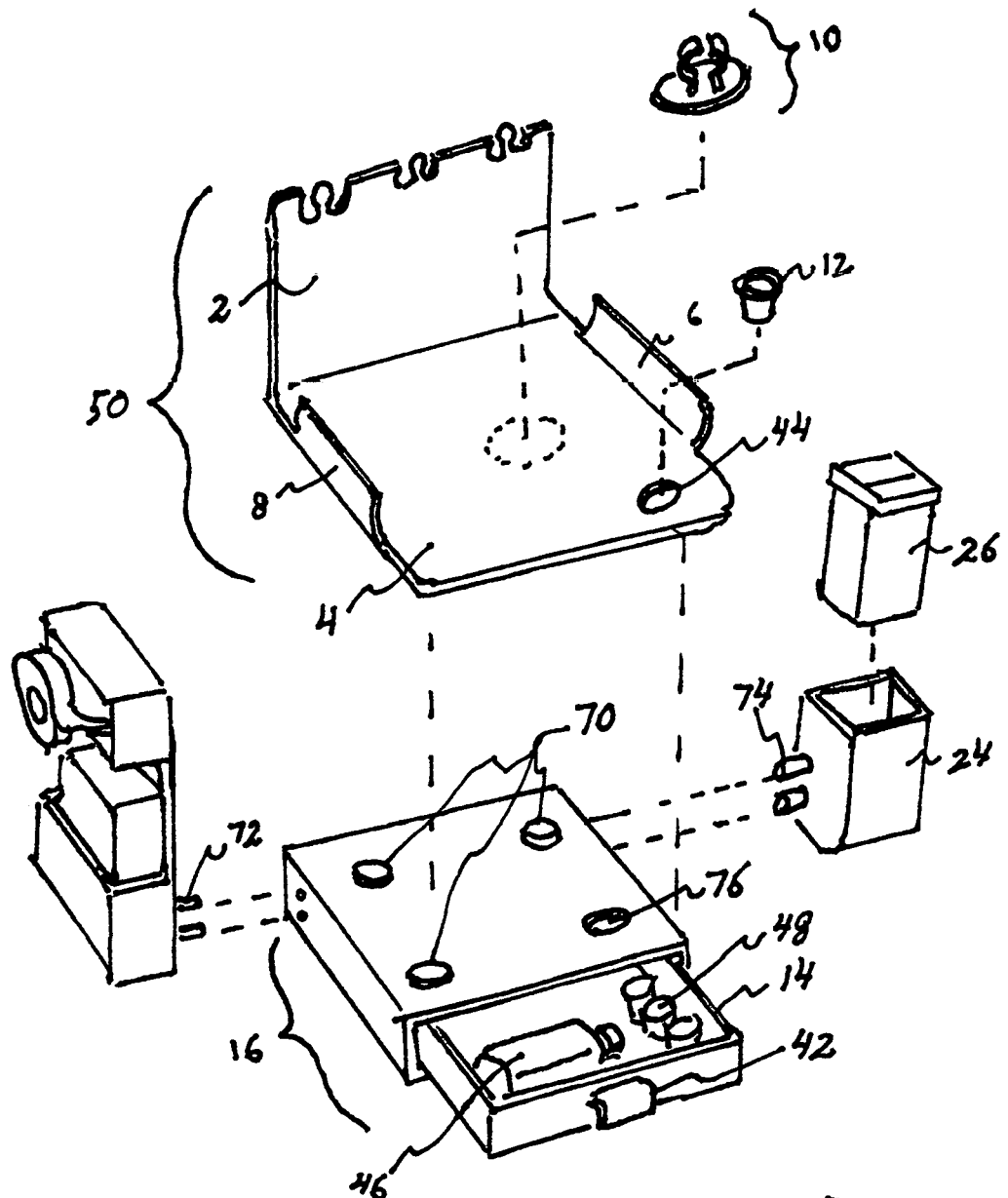
FIG. 3 is an exploded view of the invention.
Figure 4:
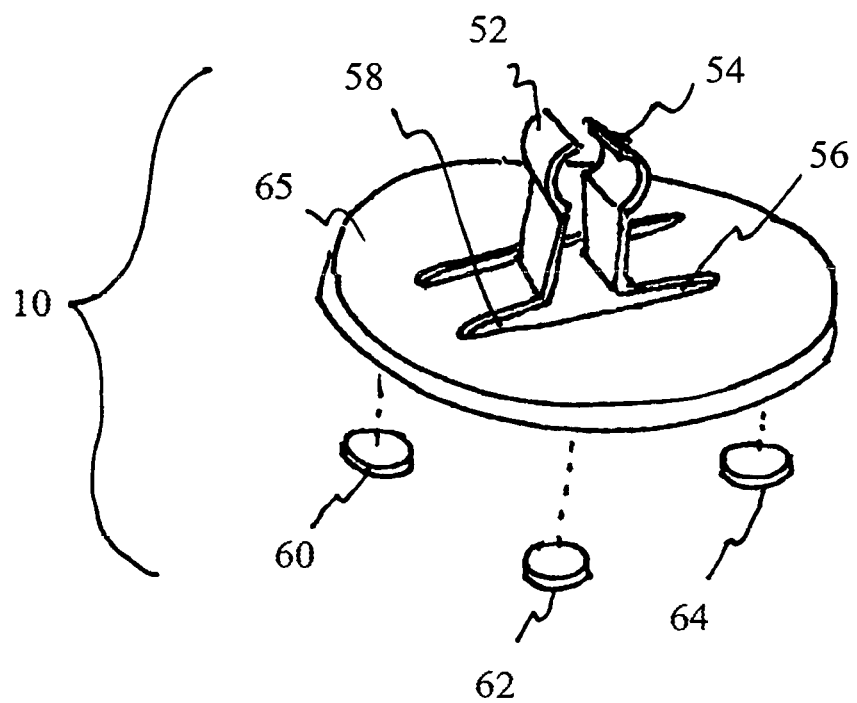
FIG. 4 is a detailed perspective view of the IV tip holding assembly of the invention.

Referring now to FIG. 1 we see a perspective view of the present invention. 100. A base portion 4 and a back portion 2 form an L shape 50 as shown in FIG. 3. Referring back to FIG. 1, The base 4 portion sits on top of a drawer assembly 16. The drawer 14 can be pulled out by pull knob 42. The drawer 14 can hold accessories used in the process of injecting drugs in IV bags such as one-ounce disposable cups 46 and a bottle of isopropyl alcohol as shown in FIG. 3. The L shaped base and back plate are made of stainless steel. The bend point is preferably radiused to allow for easy cleaning. Side walls 6, 8 help retain items located on the base plate 4. Retaining posts 18, 20, 22 located at the top of back plate 2 allow the user to hang the back end of an IV bag 40 onto a post and to secure the front drug insertion portion 42 into a holder 10 which is magnetically held to the base portion 4. The use of a plurality of holding posts 18, 20, 22 allows the user to decide where to place the IV bag depending on whether the user is left handed or right handed. A used needle container 26 is held in a cup shaped holder 24 mounted to the right side of the back plate 2. Another holding assembly 30 is mounted to the left side of the back plate 2. The holding assembly 30 includes, but is not limited to, an alcohol wipe holder 35 holding wipes 38, a lint free wipe holder 32 holding lint free wipes 34, a tape holder and dispenser 36 mounted to the side wall of holder 35.

Figure 2:
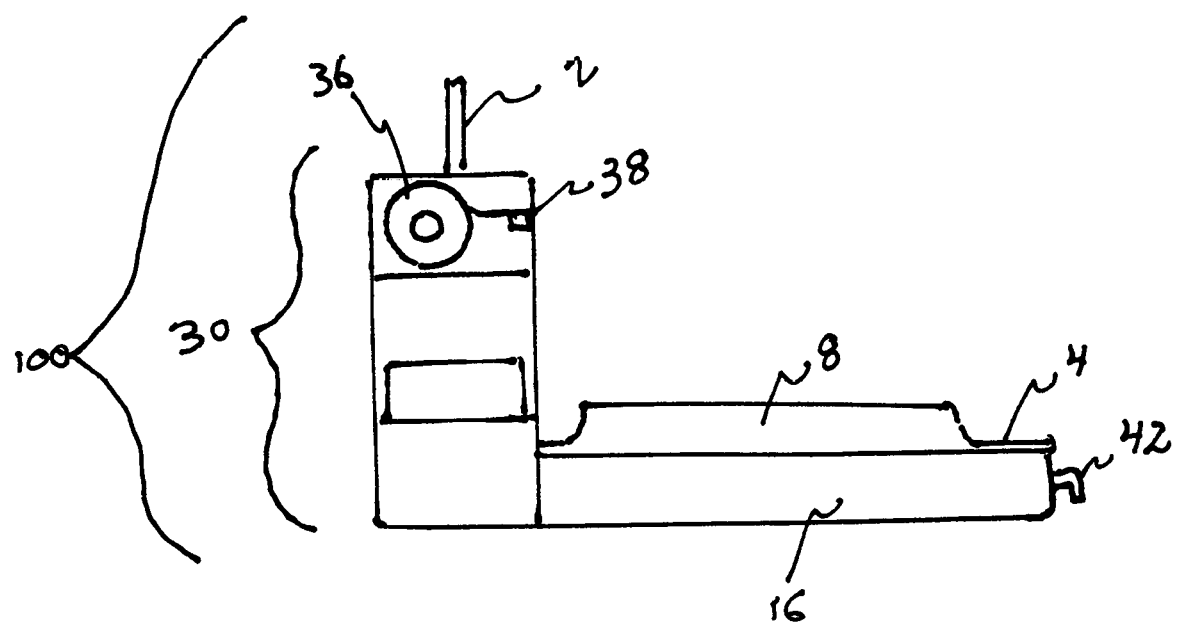
FIG. 2 is a side section view of the invention.

FIG. 2 is a side view of the invention 100. Left side holder assembly 30 can be seen. Tape holder 36 includes a tape dispensing and cutting member 38.

FIG. 3 is an exploded view of the invention. L shaped floor and base members 50 are held onto the top of the drawer assembly 16 by magnets 70. Left side holder assembly 30 is held onto drawer assembly 16 by connecting posts 72. Right side holder 24 is held onto drawer assembly side 16 by posts 74. Cup 12 can be inserted into aperture 76 and be used to catch excess liquid during the drug insertion process. IV tip holder 10 is mounted to the base member 4 and held magnetically.

Figure is an enlarged perspective view of the IV tip holder. Tip retaining arms 52, 54 are spring biased due to slots 56, 58 which allows them to be pulled away from each other during insertion of an IV bag tip and then to snap back into place to hold the tip securely. The IV tip holder 10 includes magnets 60, 62, 64 mounted to the underside of the main plate 65 so that the IV tip holder 10 can be mounted anywhere on the base plate member 4 as needed.

The entire assembly 100 is relativity inexpensive to manufacture in comparison to pharmacy grade clean areas for injecting drugs into IV bags, thereby making it more of an option for multiple units to be used in hospital rooms or other medical facility locations.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A clean environment for mixing injectable drugs comprising:
    a floor member and back member forming an L shape when viewed from a side;
    a plurality of holding compartments;
    a magnetically attached IV tip support member;
    and a drawer assembly member;
    said L shaped floor and back member positioned above said drawer assembly member;
    said holding compartments fixedly positioned on either side of said back member;
    the IV tip support assembly including spring biased support arms and a magnetic base;
    said L shaped floor and back member made of stainless steel;
    said IV tip support assembly capable of being removably retained by a magnetic base.

2. A clean environment for mixing injectable drugs as claimed in claim 1 further comprising an aperture located in said floor member capable of removably retaining a standard one ounce plastic cup.

3. A clean environment for mixing injectable drugs as claimed in claim 1 wherein said back member includes a plurality of integral support posts capable of removably retaining a rear end of a standard IV bag.

4. A clean environment for mixing injectable drugs as claimed in claim 1 wherein said holding compartments are sized for holding items which include but are not limited to a sharps needle containment box, a plurality of sanitary alcohol wipes, a plurality of lint free wipes, a roll of tape and a roll of peel off labels.

5. A clean environment for mixing injectable drugs as claimed in claim 1 wherein said drawer assembly member includes a pull out drawer surrounded by a rectilinear housing;
    said drawer sized to accommodate accessory items including but not limited to disposable one-ounce plastic cups and a bottle of denatured alcohol;
    and a top panel of said rectilinear housing includes a plurality of magnets capable of magnetically engaging an underside of said base portion.

\* \* \* \* \*